(12) United States Patent
Ghaem et al.

(10) Patent No.: US 6,285,899 B1
(45) Date of Patent: Sep. 4, 2001

(54) REMOTELY INTERROGATED BIOMEDICAL SENSOR

(75) Inventors: Sanjar Ghaem, Palatine; Iwona Turlik, Barrington, both of IL (US)

(73) Assignee: Motorola, Inc., Schaumburg, IL (US)

( * ) Notice: Subject to any disclaimer, the term of this patent is extended or adjusted under 35 U.S.C. 154(b) by 0 days.

(21) Appl. No.: 09/252,172

(22) Filed: Feb. 18, 1999

(51) Int. Cl.$^7$ .................................. A61B 5/0408
(52) U.S. Cl. ..................... 600/391; 600/392; 600/393; 600/509; 128/903
(58) Field of Search ............... 600/372, 391–393, 600/509, 547; 128/903

(56) References Cited

U.S. PATENT DOCUMENTS

| | | | |
|---|---|---|---|
| 3,253,588 | * 5/1966 | Vuillemier et al. | 128/903 |
| 3,943,918 | * 3/1976 | Lewis | 128/903 |
| 4,121,573 | * 10/1978 | Crovella et al. | 600/382 |
| 4,458,696 | * 7/1984 | Larimore | 607/152 |
| 5,168,874 | * 12/1992 | Segalowitz | 128/903 |
| 5,634,468 | * 6/1997 | Platt et al. | 128/903 |
| 5,704,352 | * 1/1998 | Tremblay et al. | 128/903 |
| 5,957,854 | * 9/1999 | Besson et al. | 600/509 |

* cited by examiner

*Primary Examiner*—Lee Cohen
(74) *Attorney, Agent, or Firm*—Douglas D. Fekete

(57) ABSTRACT

A self-contained remotely interrogated biomedical sensor (10) includes an on-board regenerative power source (52/54), data processing capability (42) and data transmission capability (42). The sensor (10) is adapted to be secured to a subject and interrogated remotely using radio-frequency technology. The present invention is applicable for use with any sensing device (76) that is capable of providing a signal in response to being placed in thermal, electrical, chemical, acoustical or otherwise in contact with the subject.

2 Claims, 4 Drawing Sheets

REMOTELY INTERROGATED BIOMEDICAL SENSOR

FIELD OF THE INVENTION

The present invention relates generally to biomedical sensors, and more particularly, the present invention relates to a remotely interrogated biomedical sensor.

BACKGROUND OF THE INVENTION

Sensing devices for use in the medical arts are well-known. For example, sensors are frequently used to observe the function of a subject's heart by detecting the sound and electrical impulses it emits. Anyone who has undergone a heart stress test has been fitted with several sensors to observe heart function, respiration, body temperature, and the like during the course of the test. Ten sensors or more are frequently used in such a test. Each sensor is coupled by a hard-wired connection extending from the sensor to a monitoring unit, i.e., at least one wire physically connecting each sensor and the monitoring unit, and each sensor provides a substantially continuous analog signal to the monitoring unit. Within the monitoring unit, the signals from each of the sensors are amplified and conditioned to provide corresponding data signals, which may then be recorded and/or observed during the test.

To securely attach the sensors to the subject each is first bonded or coupled to a suction cup or similar attaching pad. The suction cup provides the attaching force for securing the sensor to the subject in conjunction with an adhesive or tackifying agent. Sensor attachment often also requires the removal of any of the subject's body hair in the locality of the sensor.

Unfortunately, this arrangement for attaching sensors and recording the data from the sensors causes discomfort to the subject and may further lead to data errors. The sensor attachment must be sufficient to not only support the weight of the sensor, but to also support forces introduced by the hard-wired connection. In addition to the added weight of the wire itself, there are dynamic, "tugging," forces resulting from the wires extending from the subject to the monitoring unit. The attachment is therefore made larger and more aggressive to securely attach the sensor to the subject sufficiently to sustain these additional forces. This causes discomfort to the subject in both attaching the sensors, i.e., if additional shaving or skin preparation is required, and removing the sensors.

Stringing numerous wires from the subject to the monitoring unit presents its own set of problems. The wires themselves restrict the subject's movements. During a stress test the subject is required to walk or jog on a treadmill and needs to move freely. Other subjects, such as a recovering cardiac patient, may be reclined in bed and the wires may inhibit their ability to freely and comfortably sleep restricted. The wires further lead to data errors as they are frequently the cause of the sensors becoming detached due to the added weight and tugging forces. Furthermore, data can not be collected and reported unless the subject is coupled to a monitoring unit and therefore within its close proximity.

Use of suction cups and similar attaching structures also increase the required maintenance of the sensors and the monitoring system. After each use, the suction cups must be thoroughly cleaned and sanitized before the next use. The wiring connections require periodic inspection and repair, and they may add to the setup time to ensure none of the wires interferes with the subject's movements.

Thus a need exists for a sensor that eliminates the need for aggressive attachment and which is capable of reliably reporting data therefrom.

DETAILED DESCRIPTION OF THE PREFERRED EMBODIMENTS

In accordance with the preferred embodiments of the present invention, a remotely interrogated biomedical sensor is provided as a self-contained unit. The sensor includes an on-board regenerative power source, data processing and storage capability and data transmission capability. The sensor is adapted to be secured to a subject and interrogated remotely using radio-frequency technology. The present invention is thus described in terms of several preferred embodiments relating to biomedical sensors; however, its teachings are not so limited. One of ordinary skill in the art will appreciate that the present invention has application generally where it is otherwise undesirable to provide a hard-wire connection to the sensor. Furthermore, the present invention is applicable for use with any sensor that is capable of providing a signal response to being placed in thermal, electrical, chemical, acoustical or otherwise in contact with a subject.

Figure 1:
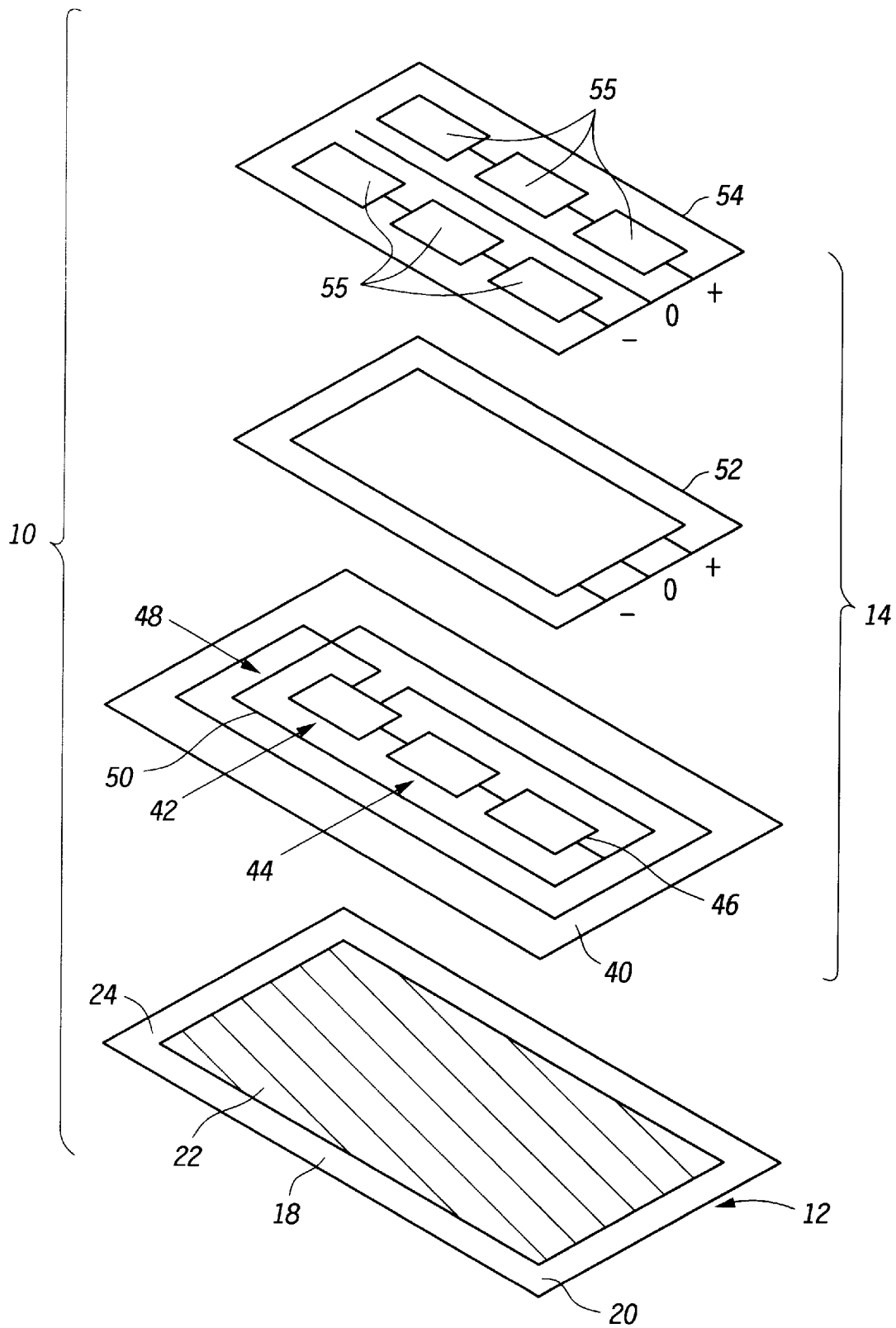
FIG. 1 is an exploded assembly view of a sensor in accordance with a preferred embodiment of the present invention.

Referring to FIG. 1, a biomedical sensor 10 includes a subject interface 12 and a sensor portion 14. Subject interface 12 is arranged to be detachably secured to a subject, and sensor portion 14 is arranged to detachably and operably secure to subject interface 12. In a preferred embodiment illustrated in FIG. 1, subject interface 12 is designed to be disposable and is formed from a thin sheet 18, such as Mylar, having a first side 20 and a second side (opposite first side 20, not depicted). Adhesive 22 is disposed in a preferred pattern on each side of sheet 18 substantially corresponding to a footprint of sensor portion 14, yet leaving a border area 24 free of adhesive. Any suitable adhesive may be used and such adhesives are well-known. Border area 24 permits, once subject interface 12 is attached to a subject, the easy removal thereof from the patient and further permits the easy removal of sensor portion 14 therefrom. The adhesive pattern also provides assistance to the user in aligning and positioning sensor portion 14 thereto. Preferably a number of subject interfaces are provided on a sheet or roll secured to a release free backing that permits individual ones to be removed and used as described.

Figure 2:
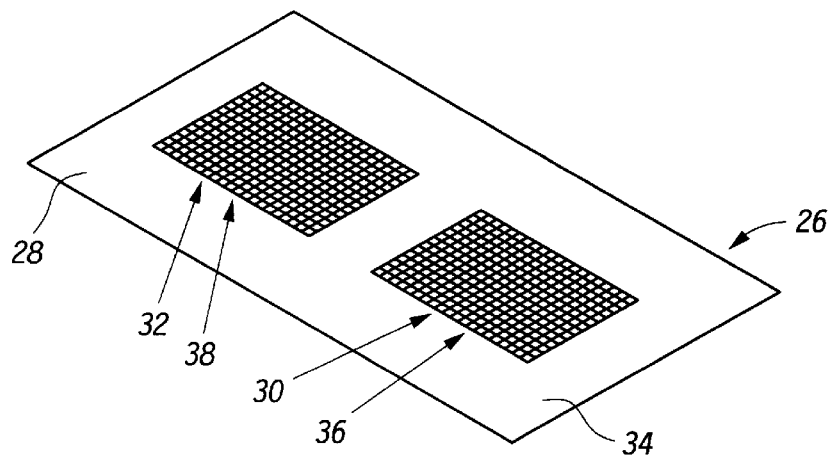
FIG. 2 is a top perspective view of a subject interface in accordance with an alternate preferred embodiment of the invention.

In certain applications it is necessary to measure the change in resistance of a subject's skin or otherwise to place sensor portion 14 in electrical contact with the subject's skin. Subject interface 26 illustrated in FIG. 2 is preferred in these applications. Subject interface 26 is also designed to be disposable and is preferably formed from a thin sheet 28 of material, such as Mylar, forming a substrate. At least one conductive pad 30, and more likely two or three such pads, such as second conductive pad 32, are formed on each of a first side 34 and a second side (not depicted). More particularly, thin sheet 28 is formed with a foraminous region 36 and conductive pad 30 is in substantial register with foraminous region 36. Conductive pad 30 is preferably formed using an isotropic conductive adhesive, and a corresponding pad is preferably formed on the second side of sheet 28 in register with foraminous region 36. Foraminous region 36 permits conductive coupling through thin sheet 28 for conductive pad 30 with its corresponding conductive pad formed on the second side. That is, conductive adhesive couples through the small holes of foraminous region 36 to provide conductive coupling of the conductive pad 30 with its corresponding conductive pad. Second conductive pad 32 is similarly formed in the vicinity of a second foraminous region 38 and is electrically coupled to a corresponding pad formed on the second side of sheet 28. In use, the conductive pads formed on the second side of sheet 28 are placed in contact with the subject's skin and adhere thereto. Conductive pads 30 and 32 remain exposed for coupling to sensor portion 14. It should be appreciated that sensor portion 14 is formed with a corresponding number of conductive pads, e.g., metalized or other conductive contacts, formed on a surface thereof for coupling to conductive pads 30 and 32.

Referring again to FIG. 1, sensor portion 14 includes a flexible substrate 40 preferably formed from a polyamide material, onto which are disposed and operably coupled a receiver/transmitter 42, a processing unit 44 and a sensing device 46. While shown as separate elements, it will be appreciated that receiver/transmitter 42, processing unit 44 and sensing device 46 may be formed in a single integrated circuit chip. Further disposed on substrate 40 are a transmit antenna 48 and a receive antenna 50, each of which are coupled to receiver/transmitter 42. A single antenna may be used for both transmit and receive, however, providing a separate transmit antenna 48 and receive antenna 50 allows for precise tuning of the antennas to the respective transmit and receive frequencies.

Further disposed on substrate 40 is at least one power source and preferably two power sources, battery 52 and solar cell array 54. As shown in FIG. 1, battery 52 and solar cell array 54 are layered onto substrate 40 creating a substantially flat and thin finished sensor product. Battery 52 may be a foil-type battery including a first and second foil electrode with a dielectric material disposed between them as are generally known. Solar cell array 54 preferably includes one or more photoelectric devices 55 coupled to provide a desired output voltage. As illustrated in FIG. 1 and in FIG. 3, each of battery 52 and solar cell array 54 provide B+ voltage and ground to a power bus structure 56 formed on substrate 40 and couples to each of the respective components thereof. In addition, battery 52 and solar cell array 54 are arranged to provide B− voltage to sensing device 46 via line 58 thereby permitting differential sensing capability.

In accordance with a preferred embodiment of the present invention, power is typically provided to the operative elements of sensor portion 14 by solar cell array 54. Output voltage from solar cell array 54 is further preferably coupled to battery 52 for providing a trickle charging current thereto providing a regenerative feature. When ambient light is unavailable to provide a sufficient output from solar cell array 54, battery 52 is then operable to power sensor portion 14.

Figure 4:
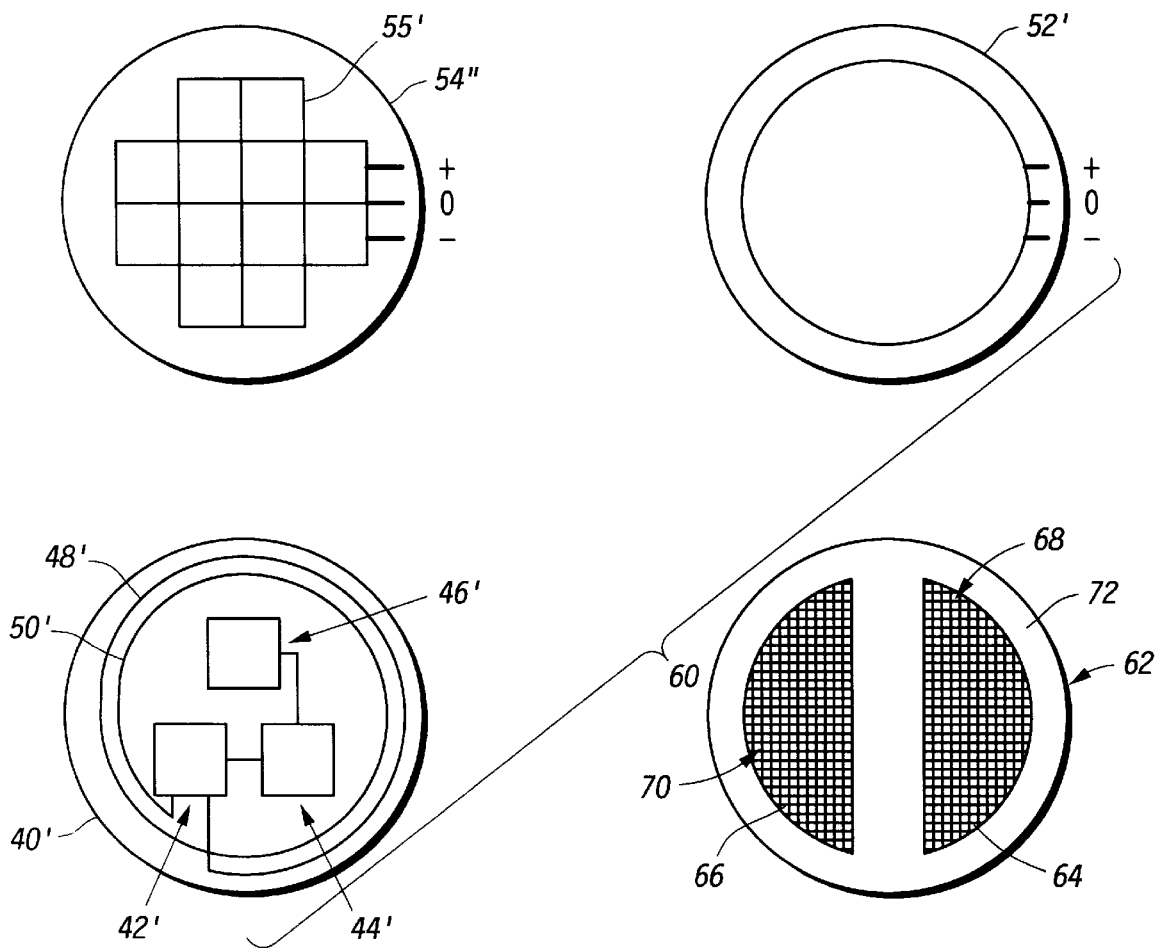
FIG. 4 is an exploded assembly view of a sensor in accordance with an alternate preferred embodiment of the present invention.

With reference now to FIG. 4, a sensor portion 60 in accordance with an alternate preferred embodiment of the present invention has a circular configuration and is otherwise formed as described with respect to sensor portion 14. Like reference numerals are used to described like elements from sensor portion 14 contained within sensor portion 60 and primed reference numerals are used to refer to like elements modified to the circular configuration. As will be appreciated, and in accordance with the present invention, a subject interface 62 is formed having a configuration corresponding to that of sensor portion 60. As shown in FIG. 4, subject interface 62 is formed with a first conductive pad 64 and a second conductive pad 66 electrically coupled to corresponding conductive pads on an opposite side of subject interface 62 via respective foraminous regions 68 and 70. Subject interface 62 further includes a border area 72 for permitting simplified attachment and removal of subject interface 62 to and from a subject and sensor portion 60. It will be appreciated that depending on a given type of sensing device 46, a subject interface such as described with respect to subject interface 12 without conductive capability may be used.

Figure 5:
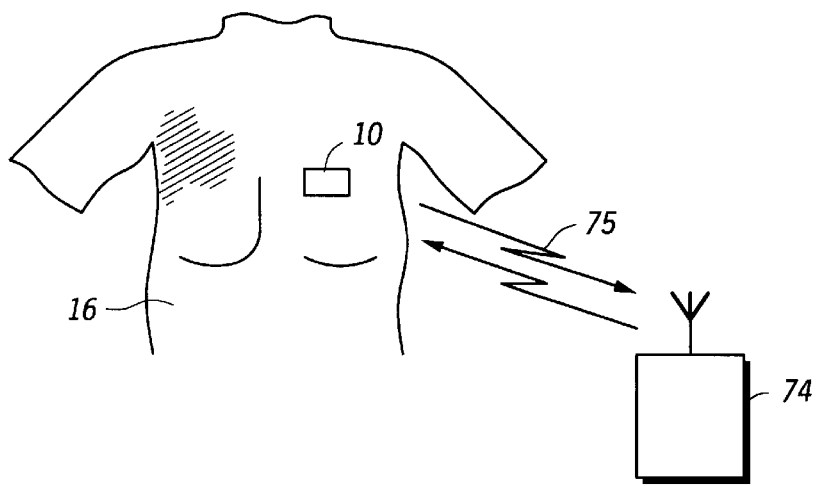
FIG. 5 is a view of a portion of the torso of a subject fitted with a sensor in accordance with a preferred embodiment of the present invention in communication with a sensor monitoring unit.

In use and with reference to FIG. 5, a sensor 10 is detachably secured to a subject 16. That is, a subject interface, such as subject interface 12 is secured to the subject and a sensor portion, such as sensor portion 14, is then secured to subject interface 12. Subject interface 12 can be secured first to sensor portion 14 and then positioned on the subject. In accordance with a preferred embodiment of the present invention, a sensor monitoring unit 74 communicates using radio-frequency transmissions 75 with sensor 10. Sensor 10 may continuously provide data, but more preferably, sensor 10 provides data in response to an interrogation signal received from monitoring unit 74.

Figure 3:
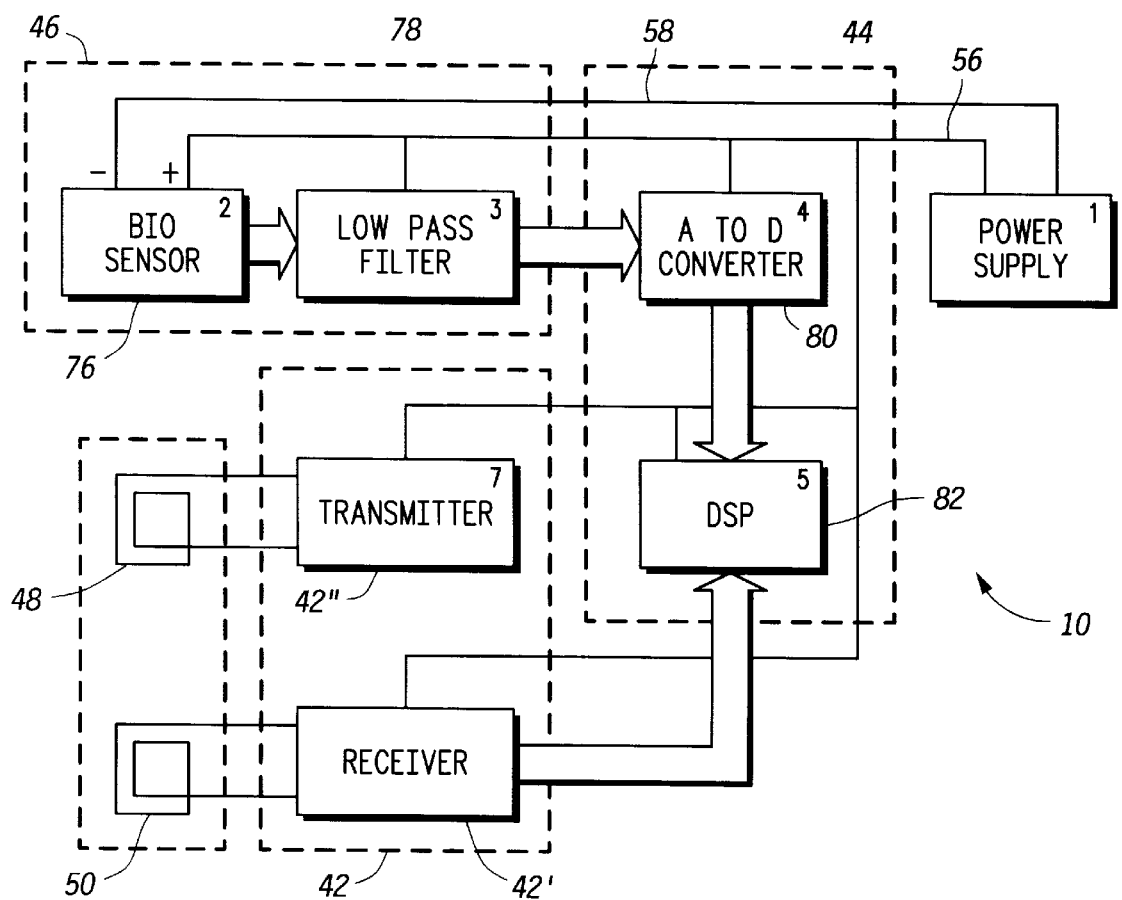
FIG. 3 is a block diagram illustration of a sensor in accordance with a preferred embodiment of the present invention.
Figure 6:
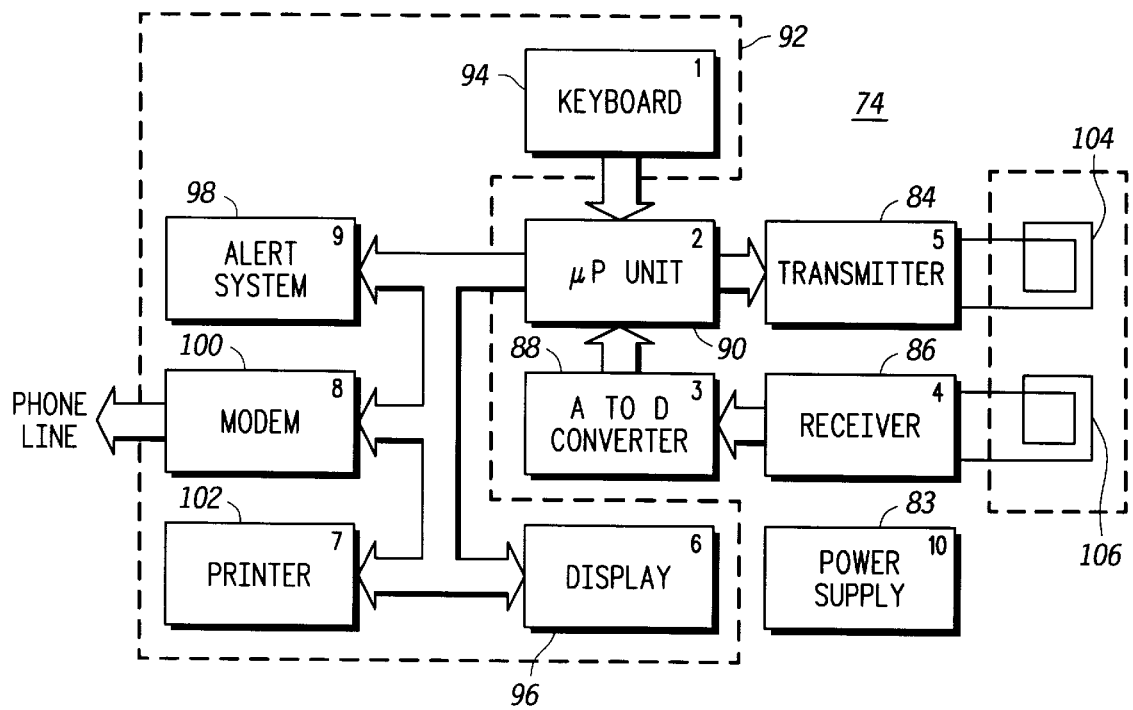
FIG. 6 is a block diagram illustration of a sensor monitoring unit in accordance with a preferred embodiment of the present invention.

With more particular reference to FIG. 3 and with reference now to FIG. 6, a preferred sensing device 46 includes a sensor element 76 and a filter 78. Filter 78 is preferably a low pass or band pass filter with filtering parameters selected to remove from the sensor signal unwanted interference, such as low frequency electrical noise from power supplies and the like and higher frequency signals such as from other types of radio frequency communication devices. Processing unit 44 preferably includes an analog-to-digital converter (ADC) 80 which is coupled to an output of filter 78 and a digital signal processor (DSP) 82. The output of filter 78, an analog signal, is converted to a digital signal within ADC 80, which is then communicated to DSP 82. DSP 82 includes program instructions to accept, process and store within its internal memory the digital sensor data. It is also programmed to receive and send signals via receiver/transmitter 42 (shown as receiver 42' and transmitter 42" in FIG. 5). Any suitable DSP may be used and programmed using its standard instruction set, and the selection and programming of DSP 82 is well within the skills of one having ordinary skill in the art.

Monitoring unit 74 preferably includes operably coupled a power supply 83, a transmitter 84, a receiver 86, an ADC 88, a DSP 90, and a user interface 92. User interface may include, but does not require each of these elements, a keyboard 94, a display 96, an interface to an alert system 98, a phone/Internet interface via a modem 100 and a printer 102. Transmitter 84 is coupled to an antenna 104 and receiver 86 is coupled to an antenna 106, although it may be possible to use a single antenna element. It is also possible that each of the elements, while shown as individual blocks, may be combined into a single integrated circuit device. As an additional alternative, a multi-purpose processor as part of computer operating a programmed set of instructions may be used as the basis for monitoring unit 74.

Each sensor 10 is provided a unique identification with respect to each other sensor 10 operating within the communication range of a monitoring unit 74. Thus, where ten sensors 10 are used on a subject, each will be assigned unique identification information which is stored within the memory of DSP 82 of the sensor. Likewise, monitoring unit 74 is programmed with the identification information for each of the sensors that it will monitor.

Figure 7:
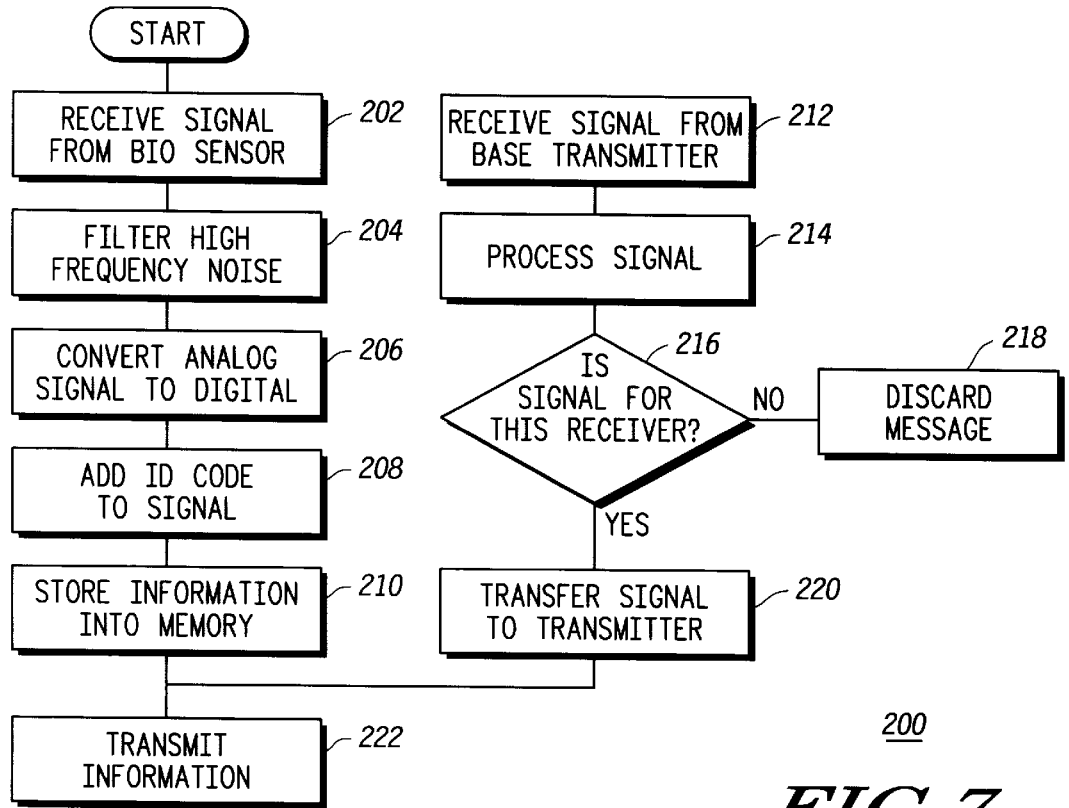
FIG. 7 is a flow diagram illustrating a method of operation of a sensor an sensor monitoring unit in accordance with a preferred embodiment of the present invention.

Referring now to FIG. 7 the method of operation of sensor 10 in conjunction with monitoring unit 74 is described with reference to the steps illustrated in flow chart 200. At step 202 analog signals are received from sensing element 76 and at step 204 are filtered by filter 78. At step 206, the filtered signals are converted to digital signals by ADC 80, and for later transmission, identification information is added to the sensor signals, step 208, forming a packet of sensor data. The packet of sensor data, at step 210, is then stored in the memory of DSP 82.

In parallel to the data collection steps 202–210, at receiver/transmitter 42, an interrogation signal is received from monitoring unit 74, step 212. At step 214 DSP 82 processes this signal, i.e., demodulates and decodes the signal to obtain the identification information contained therein. If the identification information does not match, i.e., the interrogation signal is not intended for this sensor, step 216, the message is discarded, step 218. If the message is intended for this sensor, at step 220 DSP 82 forms a transmit signal (e.g., a coded and modulated signal) containing the packet of sensor data, and at step 222 the transmit signal is transmitted to monitoring unit 74 by receiver/transmitter 42.

The present invention provides a great deal of flexibility as a biomedical sensing device. By eliminating the wire connections, the subject is free to move during the testing, Attaching the sensors to the subject is greatly simplified, and the attachments may be made smaller and less aggressive so as to reduce patient discomfort.

As described, sensors 10 preferably do not continuously transmit sensor data, but instead transmit in response to an interrogation signal. Thus, power consumption is greatly reduced. By further providing a self-sustaining power supply through the combination of battery 52 and solar cell array 54, sensors 10 may operate almost indefinitely.

The ability of sensor 10 to store and retain data provides great flexibility as does the ability to program monitoring unit 74 to selectively interrogate the sensors. Based upon the rate at which data is generated within a particular sensor, the rate at which the sensor is interrogated to transmit its data may be programmed. For example, a sensor measuring a subject's body temperature may be interrogated less frequently than a sensor measuring heart rate or brain activity. Moreover, DSP 82 may include up to and in some cases in excess of 100k of memory. Thus, sensor data may be written and retained over a long period of time and/or individual sample periods of data may be retained. In this later aspect of the invention, monitoring unit 74 may be programmed to request all data packets or selective data packets corresponding to particular sample periods. Furthermore, sensors may be worn by a subject outside the transmission/reception range of monitoring unit 74 for a period of time and the data later retrieved from the sensors.

Because each sensor is programmed with unique identification information and the ability to generate unique identification information is virtually limitless, a single subject may be provided numerous sensors and/or numerous subjects may all be provided sensors. All of these sensors may then be monitored by a single monitoring unit 74. As shown in FIG. 6, monitoring unit 74 may be provided with a variety of user interface features. This allows monitoring unit 74 to provide alerts 98, such as sounding an alarm or calling or paging an attendant, should the received sensor data fall outside a predetermined set of parameters for that data. Providing modem 100 permits the sensor data to be sent to further remote locations, and thus the sensor data may be brought to the doctor or analyst. This way the doctor may evaluate from a single location subjects being tested simultaneously at multiple locations. Of course, the data may also be simply displayed on display 96, printed in hard copy form by printer 102 or retained in some other form of storage media.

The present invention has been described in terms of several preferred embodiments directed to sensors adapted for use in biomedical applications. One of ordinary skill in the art will appreciate the invention will have application apart from the embodiments herein described, and these embodiments should not be taken as limiting of its broad teachings.

We claim:

1. A disposable interface unit for use with a remotely interrogated biomedical sensor, the biomedical sensor operatively adapted to detachably couple to the interface unit, and to transmit sensor data in response to an appropriate remotely generated interrogation signal, the disposable interface unit comprising:

a substrate comprising a first foraminous region and a second foraminous region apart from the first foraminous region, said substrate comprising a first surface and a second surface, at the first foraminous region, a conductive pad disposed on the first surface and adapted to adhesively secure to the biomedical sensor; and a conductive pad disposed on the second surface and adapted for contact to skin, said conductive pads being formed of an isotropic conductive adhesive and operatively coupled through the first foraminous region, and at the second foraminous region, a conductive pad disposed on the first surface and adapted to adhesively secure to the biomedical sensor; and a conductive pad disposed on the second surface and adapted for contact to skin, said conductive pads being formed of an isotropic conductive adhesive and operatively coupled through the second foraminous region.

2. The disposable interface unit of claim 1, wherein the substrate further comprises a border that is substantially free of adhesive.

\* \* \* \* \*